United States Patent [19]
Kruglick

[11] Patent Number: 5,632,756
[45] Date of Patent: May 27, 1997

[54] EAR CLEANING DEVICE UTILIZING BULBOUS BANDED CAGE

[76] Inventor: Kenneth Kruglick, 4217 Austin Blvd., Island Park, N.Y. 11558

[21] Appl. No.: 360,467

[22] Filed: Dec. 20, 1994

[51] Int. Cl.$^6$ .................................................. A61F 11/00
[52] U.S. Cl. .......................................... 606/162; 606/160
[58] Field of Search .............................. 606/162, 160, 606/127, 114, 113, 106

[56] References Cited

U.S. PATENT DOCUMENTS

| | | |
|---|---|---|
| 33,234 | 9/1861 | Boardman . |
| 651,395 | 6/1900 | Stapp ............................ 606/160 |
| 1,054,960 | 3/1913 | Butner ........................... 606/106 |
| 1,381,829 | 6/1921 | Hartman . |
| 1,450,612 | 4/1923 | Schultz . |
| 2,943,626 | 7/1960 | Dormia .......................... 606/127 |
| 4,046,149 | 9/1977 | Komiya ......................... 606/127 |
| 4,890,611 | 1/1990 | Monfort et al. ............... 606/160 |
| 5,334,212 | 8/1994 | Karell ............................ 606/162 |
| 5,374,276 | 12/1994 | Lay ............................... 606/162 |

FOREIGN PATENT DOCUMENTS

| | | | |
|---|---|---|---|
| 2557451 | 7/1985 | France ........................... 606/162 |
| 445683 | 6/1927 | Germany ....................... 606/162 |
| 580729 | 7/1933 | Germany ....................... 606/162 |
| 1616625 | 12/1990 | U.S.S.R. ........................ 606/160 |

*Primary Examiner*—Robert A. Hafer
*Assistant Examiner*—Benjamin K. Koo
*Attorney, Agent, or Firm*—Michael I. Kroll

[57] ABSTRACT

A disposable ear cleaning device comprising a handle and a structure on one end of the handle, for engaging, capturing and extracting ear wax located in an ear canal in an ear of a person. The structure on one end of the handle is a bulbous banded cage with different round shapes in various embodiments. In one embodiment a cotton swab is mounted on the opposite end of the handle.

2 Claims, 2 Drawing Sheets

ALTERNATE CONFIGURATION

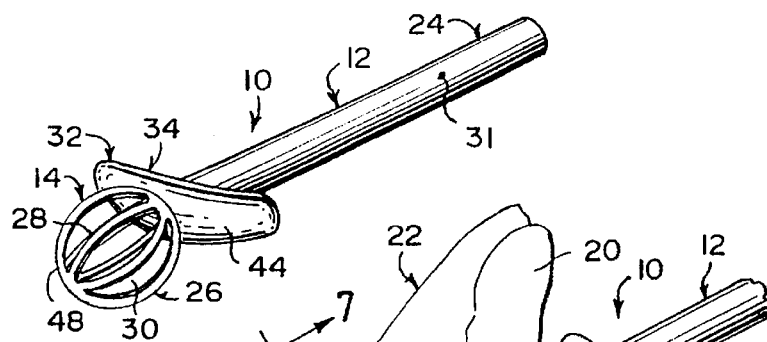
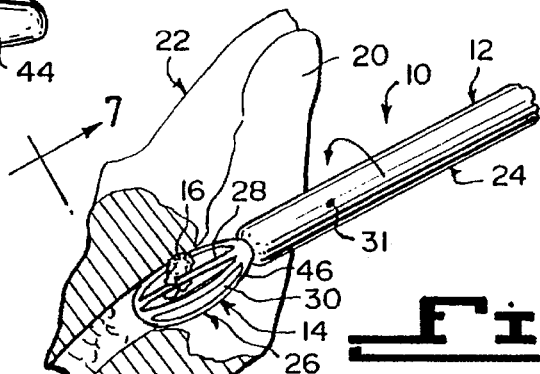
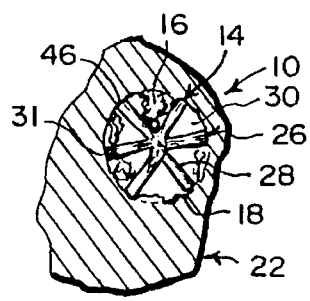
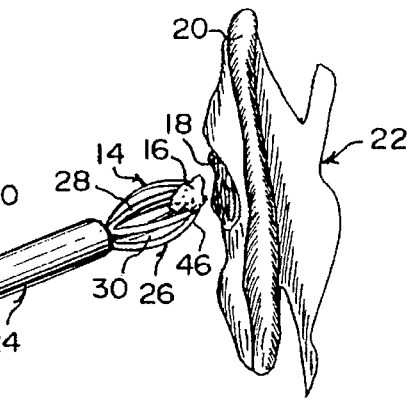
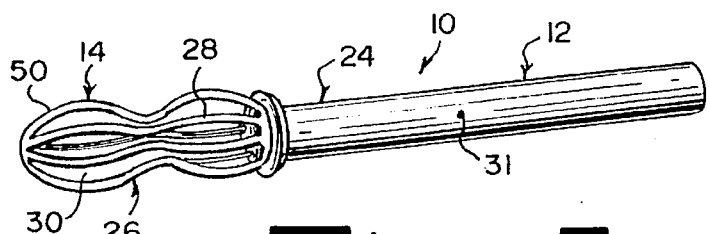

EAR CLEANING DEVICE UTILIZING BULBOUS BANDED CAGE

BACKGROUND OF THE INVENTION

1. Field of the Invention

The instant invention relates generally to human body tubular passage manipulators and more specifically it relates to a disposable ear cleaning device.

2. Description of the Prior Art

When wax build up is in an ear canal a person may try to remove the wax with a cotton tipped applicator. The person may get most of the wax out, but the wax is usually pushed farther down into the ear canal, where it becomes impacted. Adequate examination of the eardrum is impossible. A quick, painless removal of the wax by a doctor becomes difficult and frustrating. Although wax rarely causes deafness, it must be removed. If the doctor cannot remove the wax deftly the first time with a looped curette scoop, then the wax in the ear canal must be washed out. This ear enema is frightening to the person and time consuming for the doctor.

Numerous human body tubular passage manipulators have been provided in prior art that are adapted to extract materials, to massage and to generally cleanse the tubular passages in human bodies. For example, U.S. Pat. Nos. 33,234 to Boardman; 1,381,829 to Hartman; 1,450,612 to Schultz and 5,334,212 to Karell all are illustrative of such prior art. While these units may be suitable for the particular purpose to which they address, they would not be as suitable for the purposes of the present invention as heretofore described.

BOARDMAN, HENRY K. W.

IMPROVEMENT IN VAGINAL SYRINGES

U.S. Pat. No. 33,234

Improved vaginal syringe consists of a contracting and self-expanding syringe-ball attached to a hollow shaft passing through a cylinder with a sponge attachment. The sponge attachment acts as a tampon or plug in connection with the syringe-ball and shaft. The sponge is introduced into a vagina by means of the cylinder to retain an injection made by means of the syringe. This permits and insures a more perfect and complete effect of any injection so made.

HARTMAN, ROBERT R.

NOSTRIL CLEANING DEVICE

U.S. Pat. No. 1,381,829

A nostril cleaner comprising a handle and a cleaner piece connected with the handle having a continuous outer wall. A stop is at the inner end of then nostril engaging surface of the cleaner piece which limits the nostril engaging surface and the distance the cleaner piece can be inserted in the nostril. The cleaner piece is shaped to conform to the cavity of the nostril. A series of projections are on the cleaner piece between the stop and the end of the cleaner piece. The projections have blunt ends. The cleaner piece engages the lining of the nostril after being inserted its maximum distance therein and removes material from the inner surface thereof when given a rotary movement.

SCHULTZ, FREDERICK A.

EAR MANIPULATOR

U.S. Pat. No. 1,450,612

In a device of the class described, a compressible manipulating member. An extension is formed at one side of the member and has a socket opening outwardly of the free end thereof. The walls of the socket are thickened in a manner to provide a restricted opening at the outer end thereof. A reversible rigid handle is for the member. The handle has headed ends adapted to be selectively engaged in the socket and to have the thickened wall portions thereof to contract there-around.

KARELL, MANUEL L.

EAR WAX EXTRACTOR WITH DEPTH CONTROL

U.S. Pat. No. 5,334,212

The Humble Wax Remover TM—a safe ear wax extractor is composed of two parts, a safety stopper and a loop curette wax extractor. The second part is inserted into the first part, thereby making a functional unit. The entire unit is then placed into an ear canal. Once the unit is inserted into the canal, a handle is rotated, wax is caught in the loop currette and then the unit is extracted from the canal. Wax is thereby safely extracted from the ear canal. Reinsertion is done until all wax is extracted. Readjustment of depth of insertion is accomplished by changing position of the safety stopper with the loop curette wax extractor. Wax is thereby extracted without visualization of ear drums and thereby can be accomplished by lay persons.

SUMMARY OF THE INVENTION

A primary object of the present invention is to provide an ear cleaning device that will overcome the shortcomings of the prior art devices.

Another object is to provide a disposable ear cleaning device that will dislodge ear wax from within an ear canal, capture the ear wax and then remove the ear wax from the ear canal.

An additional object is to provide a disposable ear cleaning device in which a malleable bulbous cage curette head is utilized on an end of a shaft to dislodge, capture and remove the ear wax from the ear canal in a safe manner.

A further object is to provide a disposable ear cleaning device that is simple and easy to use.

A still further object is to provide a disposable ear cleaning device that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein:

FIG. 5 is a front perspective view of a third embodiment of the instant invention.

FIG. 6 is a diagrammatic cross sectional view of the ear showing the extractor head of the first embodiment being inserted and rotated into the ear canal.

FIG. 7 is a diagrammatic cross sectional view taken along line 7—7 in FIG. 6.

FIG. 8 is a rear perspective view of the first embodiment removed from the ear canal with some of the ear wax captured in the extractor head.

FIG. 9 is a front perspective view of a fourth embodiment of the instant invention.

Similar reference characters denote corresponding features consistently throughout the attached drawings.

DETAILED DESCRIPTION OF THE PREFERRED EMBODIMENTS

Figure 1:
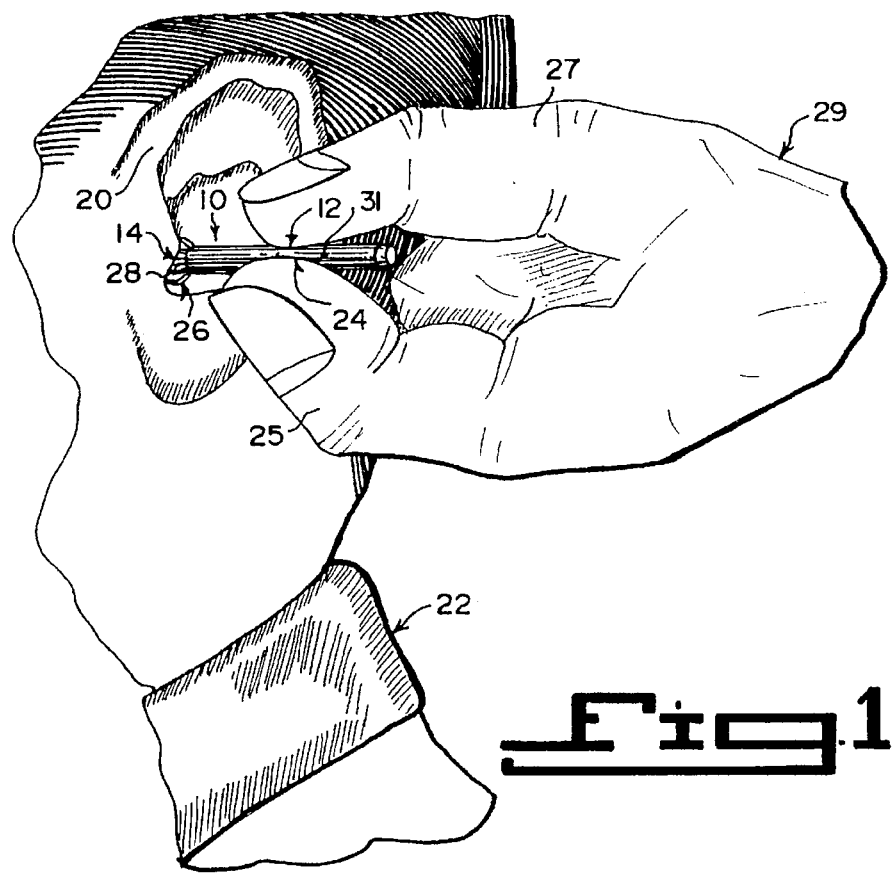
FIG. 1 is a rear perspective view of a first embodiment of the instant invention being inserted into an ear canal in an ear of a person.
Figure 2:
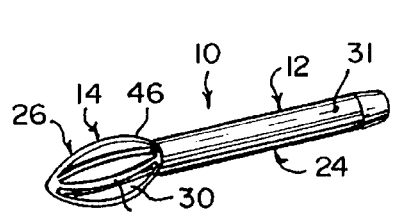
FIG. 2 is a front perspective view of the first embodiment per se.

Turning now descriptively to the drawings, in which similar reference characters denote similar elements throughout the several views, FIGS. 1 through 9 illustrate a disposable ear cleaning device 10 comprising a handle 12 and a structure 14 on one end of the handle 12, for engaging, capturing and extracting ear wax 16 located in an ear canal 18 in an ear 20 of a person 22.

The handle 12 is a rigid cylindrical member 24 that is grasped by a thumb 25 and index finger 27 of a hand 29 to insert the structure 14 into the ear canal 18, to rotate the structure 14 in the ear canal 18 to capture the ear wax 16 and remove the structure 14 with the ear wax 16 from the ear canal 18.

The engaging, capturing and extracting structure 14 is a malleable bulbous shaped curette head 26. The malleable bulbous shaped curette head 26 is a multiple banded cage 28 having openings 30 therebetween. The ear wax 16 will enter into and engage with the multiple banded cage 28, so that the ear wax 16 can be removed from the ear canal 18. The rigid cylindrical member 24 and the multiple banded cage 28 are integral and fabricated out of plastic material 31.

Figure 3:
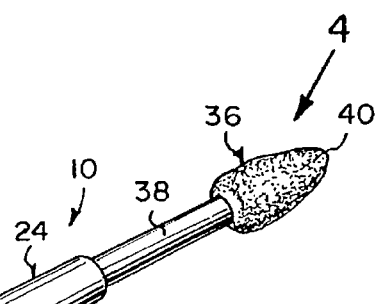
FIG. 3 is a front perspective view of a second embodiment of the instant invention.
Figure 4:
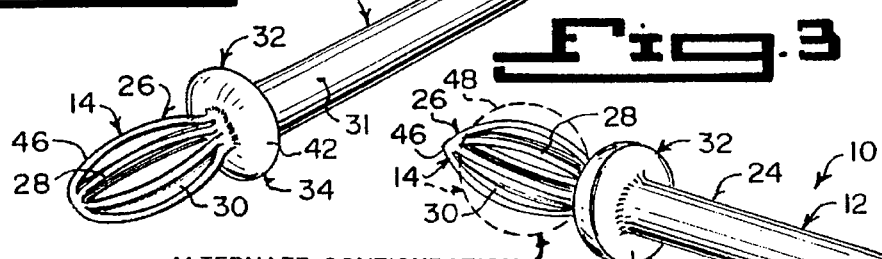
FIG. 4 is a rear perspective view taken in the direction of arrow 4 in FIG. 3, showing in dotted an alternate configuration of the extractor head.
Figure 4:
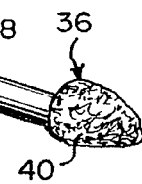

As shown in FIGS. 3, 4 and 5, a component 32 is for controlling a depth of insertion of the multiple banded cage 28 into the ear canal 18. The insertion controlling component 32 is a safety stop shield 34 between the rigid cylindrical member 24 and the multiple banded cage 28. The rigid cylindrical member 24, the multiple banded cage 28 and the safety stop shield 34 are integral and fabricated out of the plastic material 31.

In FIGS. 3 and 4, an assembly 36 is on a second end of the handle 12 for cleaning the ear canal 18 in the ear 20 of the person 22. The cleaning assembly 36 includes a shank 38 extending from the second end of the handle 12. A cotton swab 40 is on a distal end of the shank 38.

The safety stop shield 34 in FIGS. 3 and 4, is in a generally round shaped configuration 42. The safety stop shield 34, as shown in FIG. 5, is in a generally oval shaped configuration 44.

The multiple banded cage 28 in FIGS. 2 to 4 and 6 to 8, is in a generally oval shaped configuration 46. The multiple banded cage 28 in FIGS. 4 and 5, is in a generally spherical shaped configuration 48. In FIG. 9, the multiple banded cage 26 is in a generally peanut shaped configuration 50.

OPERATION OF THE INVENTION

To use the disposable ear cleaning device 10, the following steps should be taken:

1. Grasp the rigid cylindrical member 24 by the thumb 25 and index finger 27 of the hand 29, as shown in FIG. 1.
2. Insert the multiple banded cage 28 into the ear canal 18, as shown in FIGS. 1 and 6.
3. Make sure that the multiple banded cage 28 does not probe the eardrum. This can be accomplished with the safety stop shield 34.
4. Rotate the rigid cylindrical member 24, so that the openings 30 in the multiple banded cage 28 will pick up the ear wax 16 in the ear canal 18, as shown in FIGS. 6 and 7.
5. Pull the rigid cylindrical member 24 back so that the multiple banded cage 28 will exit the ear canal 18, as shown in FIG. 8.

LIST OF REFERENCE NUMBERS 10 disposable ear cleaning device
12 handle of 10
14 engaging capturing and extracting structure of 10
16 ear wax
18 ear canal
20 ear
22 person
24 rigid cylindrical member for 12
25 thumb
26 malleable bulbous shaped curette head for 14
27 index finger
28 multiple banded cage for 26
29 hand
30 opening
31 plastic material
32 insertion controlling component
34 safety stop shield for 32
36 cleaning assembly
38 shank of 36
40 cotton swab of 36
42 generally round shaped configuration for 34
44 generally oval shaped configuration for 34
46 generally oval shaped configuration for 28
48 generally spherical shaped configuration for 28
50 generally peanut shaped configuration for 28

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A disposable ear cleaning device comprising:

a) an extended rigid cylindrical handle for grasping and being rotated;

b) means on one end of said handle, for engaging, capturing and extracting ear wax located in an ear canal of a person comprising a malleable uniform bulbous shaped curette head made up of a multiple banded cage extending over the leading edge and the sides thereof having openings therebetween to capture said ear wax for removal;

c) means for controlling a depth of insertion of said multiple banded cage into the ear canal comprising a safety stop shield between said rigid cylindrical member and said multiple banded cage, said handle, multiple banded cage, and safety stop shield being integral and fabricated out of plastic material; and d) means on a second end of said handle for cleaning the air canal in the ear of the person comprising a cotton swab.

2. A disposable ear cleaning device as recited in claim 1, wherein said multiple banded cage is in a generally peanut shaped configuration.

* * * * *